United States Patent
Koops et al.

(10) Patent No.: US 6,967,714 B2
(45) Date of Patent: Nov. 22, 2005

(54) METHOD FOR DETERMINING A REFRACTIVE INDEX

(75) Inventors: Hans W. P. Koops, Ober-Ramstadt (DE); Alexander Kaya, Darmstadt (DE); Ottokar Leminger, Darmstadt (DE)

(73) Assignee: NaWoTec GmbH, Rossdorf (DE)

( * ) Notice: Subject to any disclaimer, the term of this patent is extended or adjusted under 35 U.S.C. 154(b) by 307 days.

(21) Appl. No.: 10/240,221

(22) PCT Filed: Mar. 24, 2001

(86) PCT No.: PCT/EP01/03386

§ 371 (c)(1),
(2), (4) Date: May 22, 2003

(87) PCT Pub. No.: WO01/73404

PCT Pub. Date: Oct. 4, 2001

(65) Prior Publication Data

US 2003/0179365 A1 Sep. 25, 2003

(30) Foreign Application Priority Data

Mar. 27, 2000 (DE) .......................................... 100 14 816

(51) Int. Cl.⁷ .............................................. G01N 21/41
(52) U.S. Cl. ...................................................... 356/128
(58) Field of Search ................................ 356/128–137, 356/73.1

(56) References Cited

U.S. PATENT DOCUMENTS 4,636,236 A * 1/1987 Glessner et al. .............. 65/428
5,337,185 A 8/1994 Meier et al.
5,365,329 A * 11/1994 Svendsen .................... 356/73.1
5,365,541 A 11/1994 Bullock
5,426,505 A * 6/1995 Geiser et al. ................ 356/517
5,502,560 A 3/1996 Anderson et al.
5,561,515 A * 10/1996 Hairston et al. .............. 356/28
5,910,842 A 6/1999 Piwonka-Corle et al.
6,002,522 A 12/1999 Todori et al.

FOREIGN PATENT DOCUMENTS

| DE | 40 18 664 | 1/1992 |
| DE | 198 24 624 | 2/1999 |
| WO | WO 00/35002 | 6/2000 |

* cited by examiner

*Primary Examiner*—Hoa Q. Pham
(74) *Attorney, Agent, or Firm*—Woodling, Krost and Rust

(57) ABSTRACT

The matter for which the refractive index is to be determined, is made available in the form of a theoretically determinable scattering or diffraction pattern. Two or more orders of diffraction may then be defined to form at least one intensity ratio. At least one intensity distribution may be formed by irradiating the scattering pattern using one light beam of a defined shape. Subsequently thereto, the intensity ratio may be formed based on the orders of diffraction of the intensity distribution. In addition, at least one portion of a characteristic curve may be determined, which represents the dependency of the intensity ratio on the refractive index, and, with whose assistance, the corresponding refractive index can be assigned to the intensity ratio formed.

16 Claims, 3 Drawing Sheets

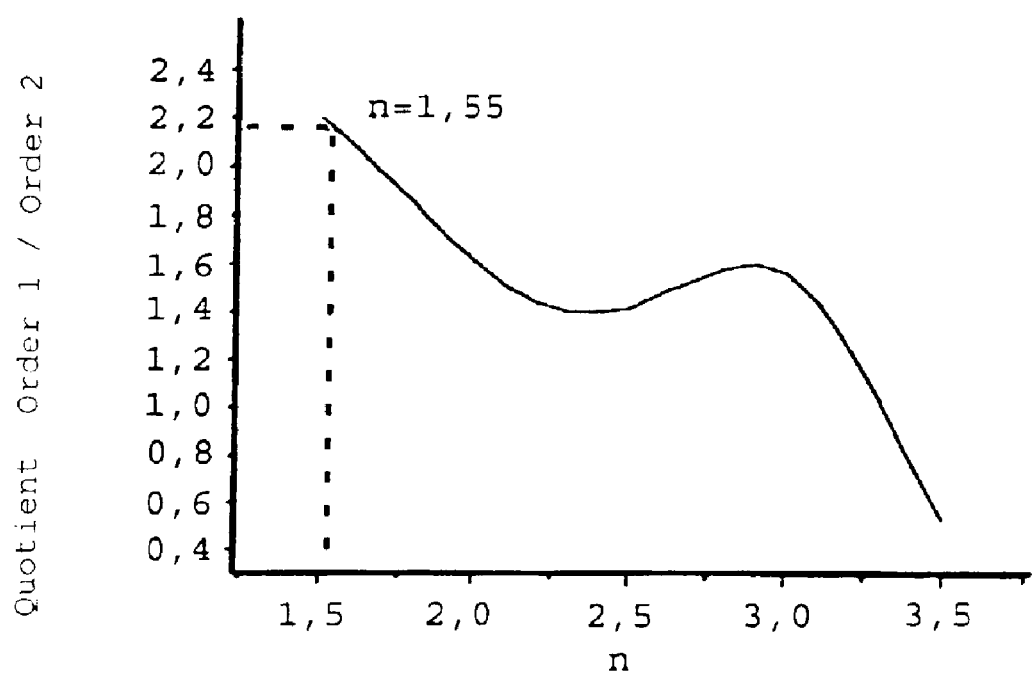

US 6,967,714 B2

METHOD FOR DETERMINING A REFRACTIVE INDEX

FIELD OF THE INVENTION

The present invention relates to a method and a device for implementing the method for determining a refractive index. The present invention further relates to a method for determining a refractive index for the smallest material quantities or material structures.

BACKGROUND INFORMATION

Some methods are available for determining the refractive index. In these methods, the refractive index may be measured using ellipsometry, or by determining the critical angle of the total reflection, or internal reflection, at or off of layers, or by employing other methods based on the refraction of the light.

When working with the smallest material quantities, whose structural dimensions vary within the micrometer or nanometer range, the available methods for determining refractive indices can fail. For example, because of insufficiently concentrated exciting radiation and improper detection of the scattered or deflected radiation, existing methods are not suitable for amounts of matter constituted as rods, whose diameter is less than 50 micrometers. Particular difficulties arise when the matter only exists in quantities whose dimensions are less than the wavelength. This is true of certain types of material, such as photonic crystals, which can be fabricated using additive nanolithography methods, including corpuscular beam-induced deposition.

SUMMARY OF THE INVENTION

Exemplary embodiments and/or exemplary methods of the present invention are directed to providing a device and a method, inter alia, for determining the refractive index of material quantities or amounts of matter or of material structures in the micrometer range.

In further exemplary embodiments and/or exemplary methods of the present invention, the matter for which the refractive index is to be determined may be made available in the form of a theoretically determinable scattering or diffraction pattern. Two or more orders of diffraction may then be defined to form at least one intensity ratio. At least one intensity distribution may be formed by irradiating the scattering pattern using one light beam of a defined shape. Subsequently thereto, the intensity ratio may be formed based on the orders of diffraction of the intensity distribution. In addition, at least one portion of a characteristic curve may be determined, which represents the dependency of the intensity ratio on the refractive index, and, with whose assistance, the specific intensity ratio may be assigned to the corresponding refractive index.

In further exemplary embodiments and/or exemplary methods of the present invention, the intensity ratio may be assigned to a refractive index, it may be checked whether the intensity ratio formed may be uniquely assigned to a refractive index using the characteristic curve. If this is not the case, it may be necessary to likewise implement the method steps until the intensity ratio is formed for one or more amounts of matter of another optical density. However, step b) may be retained. Again using the characteristic curve, corresponding refractive indices may then likewise be assigned to the intensity ratios of the other amounts of matter. The refractive index sought may then be selected or determined by comparing the other measuring, or test, points to the measuring point that is not to be uniquely assigned.

For what appears to be the first time, the described method and device of the present invention can make it possible to determine the refractive index in a simple manner, in particular for the smallest material quantities or structures of matter.

Further exemplary embodiments and/or exemplary methods of the present invention are provided to use a light beam in the form of a Gaussian beam. The only local action of the Gaussian beam may have the highly positive effect that the intensities of the diffraction maxima exhibit an intensified dependency on the properties of the matter that makes up the diffraction structure. This may be caused by the physical fact that, besides being dependent on the geometric structure of the matter, the scattering or diffraction is also dependent upon the optical density of the matter.

In further exemplary embodiments and/or exemplary methods of the present invention, to determine the intensity ratio between two diffraction maxima, higher orders of diffraction may be used. Higher-order diffraction intensities, if at all, may only have a small portion of undiffracted scattered light. Within the range of the measuring accuracy, this may not rule out using the diffraction maximum of the zeroth order and of the first order to derive one or the intensity ratio needed to determine the refractive index.

Exemplary embodiments and/or exemplary methods of the present invention are also directed to be used when the light used has a defined polarization direction. This may result in a considerable simplification, for example, when theoretically determining the diffraction intensities or their ratios. In this context, in accordance with the present invention, either TE- (transverse electric) or TM- (transverse magnetic) polarized light may be used, i.e., either horizontally or vertically polarized light.

In further exemplary embodiments and/or exemplary methods of the present invention, a diffraction grating may be used as a scattering pattern to determine the refractive index. Diffraction gratings may be able to be fabricated on an experimental basis and be able to be theoretically measured or mathematically represented relatively easily. Accordingly, in accordance with the present invention, the grid rods may contain the material to be examined for the refractive index. In further exemplary embodiments and/or exemplary methods of the present invention, the use of light having a Gaussian intensity profile may be used since, besides the features already described, this can make it possible to simplify the mathematical, i.e., numerical, determination of the diffraction intensity distribution. As a result, by using a diffraction grating, for example, a true comparison may be able to be made between the theoretically defined values and the experimental values.

In further exemplary embodiments and/or exemplary methods of the present invention, the diffraction intensities may be measured in the far field of the diffraction structure or of the grating. In this context, one was able to ascertain within the scope of the present invention that, within the range of the measuring accuracy, the assumption is justified that the scattering pattern in the form of a grating is essentially a two-dimensional structure. In other words, one may start from the assumption of an infinite linear expansion of the rods, which, in turn, may substantially simplifies the theoretical or numerical determination of the diffraction intensity distribution. In this context, far field means that the size of the grating is much smaller than the measuring, or test, distance in which the intensity maxima or intensity distribution are measured.

The measurement of the intensity ratio or of the diffraction distribution, performed within the framework of the exemplary methods and/or exemplary embodiments of the present invention, may be carried out during transmission as well as during reflection, the light transmitted by the scattering pattern being measured or detected.

Further exemplary embodiments and/or exemplary methods of the present invention may be used to determine whether the matter to be examined has a homogeneous or inhomogeneous distribution of matter. This is to be taken into consideration such as when the attempt is made, for example, when growing the grating rods, to deliberately grow them inhomogeneously. Thus, by applying the method and/or device according to the present invention, one may ascertain whether the experimental manipulations were successful with respect to the distribution of matter in the rods.

When an exemplary method and/or exemplary device according to the present invention is applied, it is not only possible to determine the real part of a refractive index, but, in the same way, it is of utmost benefit that the imaginary part of a complex refractive index may also be ascertained. To this end, in accordance with the present invention, two different intensity ratios are taken into consideration to determine each of the two unknowns of the complex number.

This case is to be distinguished from the case already described above, where, from the theoretical assignment of the experimentally determined intensity ratio, no unique way is apparently derived to make an assignment to one refractive index. The present invention may remedy such an ambiguity by carrying out or forming the intensity ratios on different scattering patterns, which should contain different distributions of matter.

Exemplary embodiments of the present invention may be a device which is suited for implementing the above-described method and, to this end may include, e.g., a device for supplying a defined light beam for irradiating diffracting and/or scattering matter, a detector device for recording a diffraction intensity distribution emanating from the matter, a device for determining the intensity ratio(s) between at least two detected diffraction maxima from the diffraction intensity distribution, and a computer device for at least partially determining the functional relationship between the intensity ratio and the refractive index and for assigning the intensity ratio to the refractive index.

BRIEF DESCRIPTION OF DRAWINGS

FIG. 5 illustrates the dependency of the quotient derived from the intensity of the first-order maximum and of the second-order maximum, on the refractive index of the grating rods.

DETAILED DESCRIPTION

Figure 1:
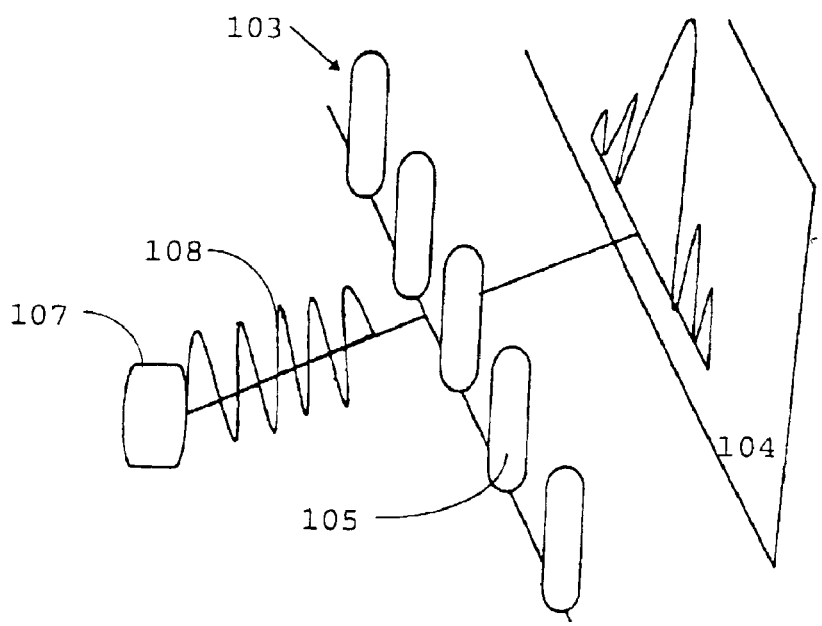
FIG. 1 shows a schematic representation of the measuring set-up for determining the intensities of the orders of diffraction.
Figure 2:
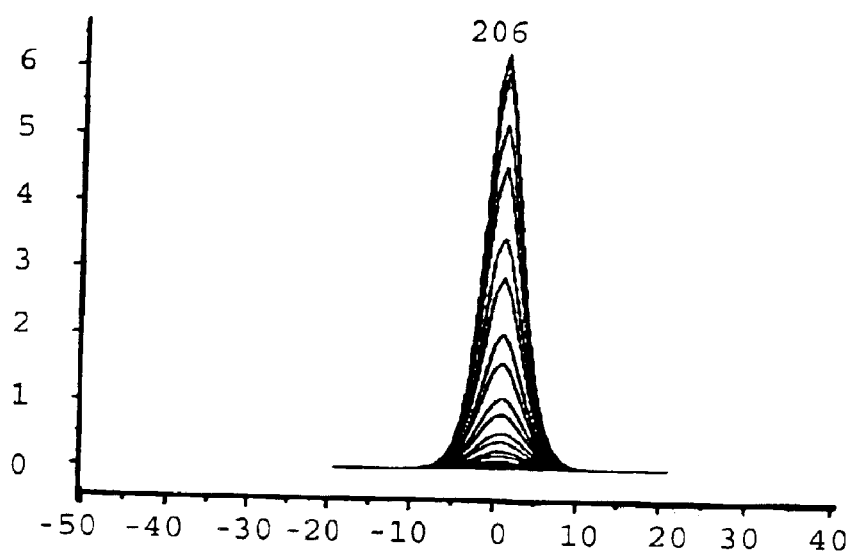
FIG. 2 shows the Gaussian intensity profile of the light used for the measurement.

In FIG. 1, a diagrammatic representation of the measuring set-up is evident, as may be used to determine the intensities of the orders of diffraction within the framework of the present invention. In this context, FIG. 1 shows a light source 107, for example, a laser, whose monochromatic light is transmitted via an optical fiber, as a spatially limited wave 108, for example in the form of a Gaussian beam 206 (FIG. 2), at diffracting material 103. Matter 103 depicted in FIG. 1 was grown in accordance with the present invention in such a way that the matter, in its geometric arrangement, forms a diffraction grating, which may be able to be easily measured or represented mathematically. The type of spatial distribution of amount of matter 103 is often referred to as a motif function. With respect to a grating arrangement 103, for example, a motif function would be understood as the spatial distribution of the matter within one grating period. Grating rods 105 are each disposed centrally in the grating period, and the length of one period corresponds to the distance between two rods 105. As the result of scattering or diffraction at matter 103, an intensity distribution of the light is generated in far field 104, which is measured there using a spatially well resolving detector. In this context, far field means that the distance between the detector and diffracting matter is much greater than the width of the grating formed by the matter. This measurement is a so-called transmission measurement, which, however, may also be replaced by a reflection measurement.

Figure 3:
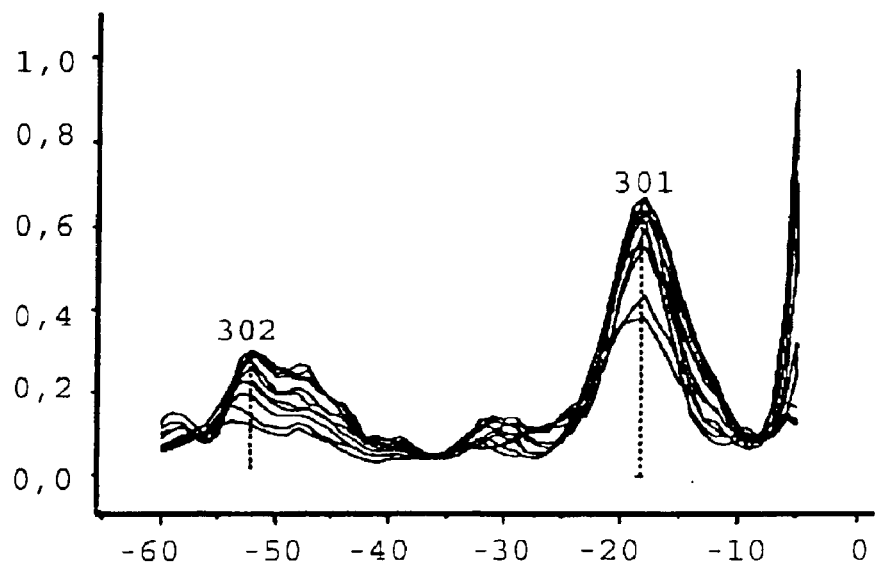
FIG. 3 illustrates a measured diffraction pattern, that was measured on a diffraction grating, whose rods are made of silicon.

A measured diffraction-intensity distribution in the far field may be seen in FIG. 3. The diagram according to FIG. 3 shows the curve shape of the diffraction maxima for various intensities of the irradiated light. In this instance, the intensity is plotted in arbitrary units over the angles of diffraction. The diffraction pattern was measured on a silicon probe having altogether 11 grating rods placed at a distance of 4 $\mu$m from one another and having a radius of 290 nm. The measuring distance to the probe was 18.5 cm. Diffraction maximum 301 of the first order and that of second order 302 are shown from right to left in the representation according to FIG. 3. In this case, the probe was irradiated by a laser beam, which was guided in an optical fiber and whose angular intensity profile may be inferred from FIG. 2. This Gaussian profile was likewise measured at a distance of 18.5 cm. The Gaussian beam had a wavelength of 1.5 $\mu$m and a half width of 5.4 $\mu$m.

Within the framework of the method according to the present invention, a numerical analysis of the intensity maxima shown in FIG. 3 yielded, inter alia, their intensity ratio. Although, for the most part, unnecessary, the ratio between the maximum of the zeroth order and that of the first order may be drawn upon as well, for example, to achieve a higher accuracy.

To derive information about the influence of the refractive index on the diffraction intensities, exemplary embodiments and/or exemplary methods of the present invention provide for using a numerical simulation to determine the diffraction intensities on the periodically refracting structure.

In this context, the simulation is based on approaches or methods of resolution for fully solving the Helmholtz equation with boundary conditions, or values. For this purpose, the following formula is used to describe the incident Gaussian beam:

$$E'(x, y) = \frac{\alpha}{\sqrt{\pi}} \int_{-\theta_{max}}^{\theta_{max}} \exp\left\{-\alpha^2 \sin^2\theta + i\frac{2\pi}{\lambda}[(x-x_G)\cos\theta + (y-y_G)\sin\theta]\right\} \cos\theta \, d\theta;$$

-continued $$\alpha = \frac{\pi w_0}{\lambda}$$

$\lambda$ ... being the wavelength of the light, $w_0$ ... the spot, or focusing or mark, width, $x_G, y_G$ ... coordinates of the center of the Gaussian beam, and the following formulation being selected for the scattered light field:

$$E^S = \sum_{m=1}^{M} E_m^S; \quad E_m^S = \sum_l t_l^{(m)} H_l^{(1)}\left(\frac{2\pi}{\lambda}r_m\right)\exp(il\varphi_m)$$

For the light field within the cylinders, i.e., of the grating rods, due to their cylindrical form, an approach including Fourrier-Bessel functions was used:

$$E_m^c = \sum_l u_l^{(m)} J_l\left(n_c \frac{2\pi}{\lambda}r_m\right)\exp(il\varphi_m)$$

In each of the approaches or methods of resolution, index m passes, in succession, over all the cylinders. Its total number being limited to M=11 in the present exemplary embodiment.

The other variables used in the approaches may be assigned as follows:

$r_m, \varphi_m$ ... local polar coordinates in the m-th cylinder
$n_c$ ... refractive index to be determined
$J_1$ and $H_1^{(1)}$ ... 1st order Bessel and Hankel functions and
$U_1^{(m)}, t_1^{(m)}$ ... complex unknown variable The following boundary conditions or values are derived from the physical fact that the transition of the light field from the outside into the cylinder takes place in both continuous as well as differentiable fashion:

$$E_m^c = E_S + E_i \quad \frac{\partial E_m^c}{\partial r} = \frac{\partial E_S}{\partial r} + \frac{\partial E_i}{\partial r}$$

It is a question in this case of altogether 2M boundary conditions, namely two for each cylinder rim. Inserting the above formulas into these boundary conditions, after a few transformations, one obtains an enormous linear complex system of equations for the unknowns $u_1^{(m)}$, $t_1^{(m)}$. The system of equations may be solved for the unknown $t_1^{(m)}$. In this manner, the desired intensities $I_S = E_S^2$ in the far field are able to be calculated for the various values of the refractive index $n_c$.

Figure 4:
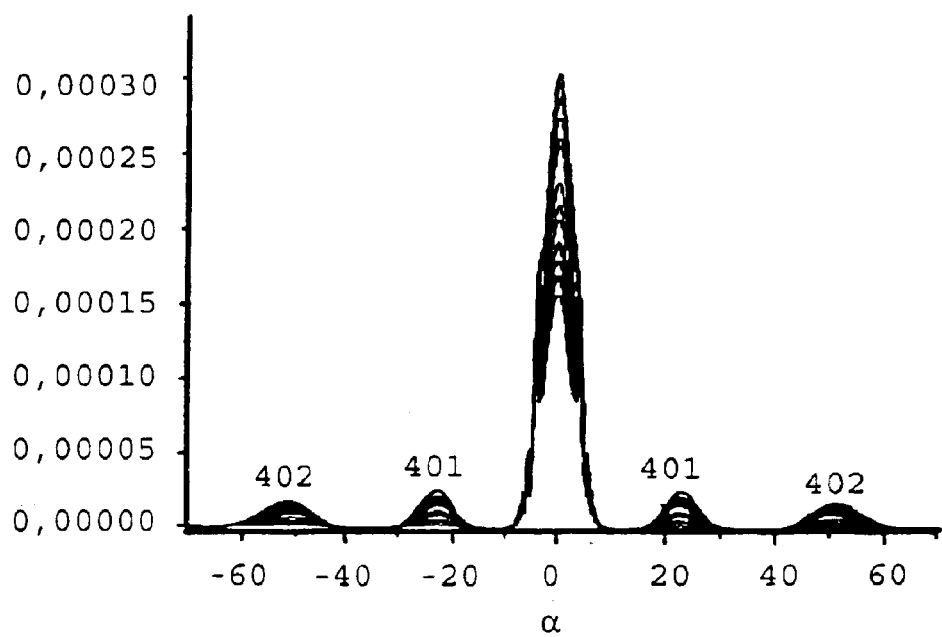
FIG. 4 shows a simulation of the diffraction pattern according to FIG. 3.

Subsequent to the simulation in accordance with the present invention, diffraction intensities may be obtained in the far field as a function of the angles of diffraction. A diffraction pattern calculated in this manner is illustrated in FIG. 4. For this simulation, the assumption was made that the irradiated light is transverse-electric light. The wavelength and the half width of the light conform with the Gaussian profile indicated above. The same also applies to the grating to be examined. From the aforesaid simulation, the quotient may now be derived from diffraction intensity 401 of the first order and from that of the second order 402, for the refractive index that taken as a basis. If the simulation is repeated for a multiplicity of different refractive indices, then the specific functional relationship between the ratio of the intensities of diffraction maxima 401, 402 and the corresponding refractive indices is able to be determined in this manner.

FIG. 5 illustrates this dependency in a diagram. The curve shape it depicts relates, in particular, to the maxima ratio of the first and second order of diffraction 401, 402 (FIG. 4) as a function of various refractive indices. As can be inferred from the curve shape, for certain intensity ratios, there are many ways to make an assignment to a refractive index. As a result, in accordance with the present invention, in order to uniquely define a refractive index for a specific material quantity, the need may arise for a plurality of measurements on probes of different optical densities. The purpose of these additional measurements may be essentially to determine the curvature characteristic of the curve defined by the functional relationship, to thereby enable the measured intensity ratio to be uniquely assigned to a refractive index.

As may be inferred from the diagram according to FIG. 5, for the material quantity examined here, given an intensity ratio of the first and second order of approximately 2.15, a refractive index of n=1.55 is ascertained.

What is claimed is:

1. A method for determining a refractive index, the method comprising:
   a) providing an amount of matter in a form of at least one pattern of a theoretically measurable diffraction pattern and a theoretically measurable scattering pattern;
   b) defining at least two orders of diffraction from the at least one pattern to form at least one intensity ratio;
   c) generating at least one intensity distribution by irradiating the at least one pattern using a light beam of a defined form;
   d) forming the at least one intensity ratio using the at least two orders of diffraction of the at least one intensity distribution;
   e) determining at least one portion of a characteristic curve of a functional relationship between the at least one intensity ratio and the refractive index; and
   f) assigning the at least one intensity ratio to the refractive index using the characteristic curve.

2. The method of claim 1, wherein step f) includes determining whether the at least one intensity ratio is uniquely assignable to the refractive index, and if not, performing the following:
   i) performing steps a) through d) of the method for another amount of matter having a different optical density than the amount of matter, retaining step b),
   ii) assigning another at least one intensity ratio to its respective another refractive index using another characteristic curve, and
   iii) assigning the respective another refractive index to the another amount of matter.

3. The method of claim 1, wherein the light beam has a Gaussian beam shape.

4. The method of claim 1, wherein the light includes at least one of monochromatic light and polarized light.

5. The method of claim 1, wherein the at least one intensity ratio is derived from higher order diffraction maxima.

6. The method of claim 1, wherein the at least one pattern is configured to include a diffraction grating.

7. The method of claim 1, wherein the at least one intensity ratio is determined from a diffraction distribution in a far field.

8. The method of claim 1, wherein the at least one pattern is configured to include an essentially two-dimensional arrangement of rods.

9. The method of claim 1, wherein one of the at least one intensity ratio and a diffraction distribution is measured during transmission and during reflection.

10. The method of claim 1, wherein the amount of matter has one of a homogeneous matter distribution and an inhomogeneous matter distribution.

11. The method of claim 1, wherein, by applying the method, the refractive index including a complex refractive index that is determinable from an imaginary part and a real part.

12. The method of claim 1, wherein the light beam of the defined form includes a Gaussian light beam of one wavelength and is directed at diffracting the amount of matter in a geometric arrangement having a mathematically representable motif function;

the at least one intensity distribution is measured in a far field, in transmission, apart from an undiffracted beam, at least one further maximum of intensities of a maxima of a zeroeth order to a first order and of the first order to a second order being formed, and these being compared to a calculated value of an intensity ratio calculated from a diffraction intensity on the geometric arrangement having the mathematically representable motif function;

the refractive index of the amount of matter is varied in the mathematically representable motif function;

the intensity ratio of the at least two orders of diffraction to the refractive index have a unique dependency; and the refractive index of the amount of matter is determinable by comparing a measured intensity ratio and the calculated value of the intensity ratio.

13. The method of 12, wherein the geometric arrangement having a mathematically representable motif function is in a form of a diffraction grating.

14. The method of claim 1, wherein the refractive index is determined for at least one of the amount of matter and a structure of matter, the matter being in a micrometer range.

15. A device for determining a refractive index for one of an amount of material and a structure of matter, in the micrometer range, the device comprising:

a beam device to supply a defined light beam to irradiate at least one of a diffracting matter and a scattering matter;

a detector device to record a diffraction intensity distribution emanating from the at least one of the diffracting matter and the scattering matter;

a determination device to determine at least one intensity ratio between at least two detected diffraction maxima from the diffraction intensity distribution of predefined orders of diffraction; and a computer device to at least partially determine a functional relationship between the at least one intensity ratio and the refractive index and to assign the respective at least one intensity ratio to the corresponding refractive index.

16. The device of claim 15, wherein the device is configured to determine a refractive index by performing the following:

a) providing an amount of matter in a form of at least one pattern of a theoretically measurable diffraction pattern and a theoretically measurable scattering pattern;

b) defining at least two orders of diffraction from the at least one pattern to form at least one intensity ratio;

c) generating at least one intensity distribution by irradiating the at least one pattern using a light beam of a defined form;

d) forming the at least one intensity ratio using the at least two orders of diffraction of the at least one intensity distribution;

e) determining at least one portion of a characteristic curve of a functional relationship between the at least one intensity ratio and the refractive index; and f) assigning the at least one intensity ratio to the refractive index using the characteristic curve.

* * * * *

UNITED STATES PATENT AND TRADEMARK OFFICE
CERTIFICATE OF CORRECTION

PATENT NO. : 6,967,714 B2
DATED : November 22, 2005
INVENTOR(S) : Hans W.P. Koops, Alexander Kaya and Ottokar Leminger It is certified that error appears in the above-identified patent and that said Letters Patent is hereby corrected as shown below:

Column 2,
Line 52, after "defined" delete "valucs" and insert -- values --.

Signed and Sealed this

Seventeenth Day of January, 2006

JON W. DUDAS
*Director of the United States Patent and Trademark Office*